United States Patent [19]

Sharma

[11] Patent Number: 4,933,339
[45] Date of Patent: Jun. 12, 1990

[54] (2-CYANO-2-ARYLETHYL)PYRIDINE COMPOUNDS USEFUL IN CONTROLLING FUNGICIDAL ACTIVITY

[75] Inventor: Ashok K. Sharma, Horsham, Pa.

[73] Assignee: Rohm and Haas Company, Philadelphia, Pa.

[21] Appl. No.: 178,739

[22] Filed: Apr. 7, 1988

Related U.S. Application Data

[63] Continuation of Ser. No. 888,773, Jul. 30, 1986, abandoned, which is a continuation-in-part of Ser. No. 767,924, Aug. 21, 1985, abandoned.

[51] Int. Cl.$^5$ ............................................. A01N 9/22
[52] U.S. Cl. .................................. 514/235.5; 544/124; 544/131; 544/333; 544/405; 546/264; 546/279; 546/281; 546/283; 546/330; 546/336; 514/256; 514/332; 514/341; 514/343; 514/357
[58] Field of Search ............... 546/330, 264, 279.281, 546/283, 336; 544/333, 405, 131, 124; 514/332, 232, 256, 237, 341, 343, 357, 235.5

[56] References Cited

U.S. PATENT DOCUMENTS

| | | | |
|---|---|---|---|
| 3,254,092 | 5/1966 | Meschino | 71/94 |
| 3,396,224 | 8/1968 | Van Heyningen | 71/94 |
| 3,397,273 | 8/1968 | Van Heuningen et al. | 514/357 |
| 3,544,682 | 12/1970 | Taylor et al. | 71/92 |
| 3,655,359 | 4/1972 | Krumkalms | 71/94 |
| 3,794,642 | 2/1974 | Kress | 71/92 |
| 3,818,009 | 6/1974 | Taylor et al. | 71/92 |
| 3,868,244 | 2/1975 | Taylor et al. | 71/92 |
| 3,869,456 | 3/1975 | Taylor et al. | 71/92 |
| 3,887,708 | 6/1975 | Taylor et al. | 71/92 |
| 4,116,665 | 9/1978 | Krumkalns | 71/94 |
| 4,224,052 | 9/1980 | Szucs | 71/105 |
| 4,313,754 | 2/1982 | Szucs | 71/94 |
| 4,366,165 | 12/1982 | Miller et al. | 548/101 |
| 4,383,848 | 5/1983 | Szucs | 71/105 |

FOREIGN PATENT DOCUMENTS

| | | | |
|---|---|---|---|
| 165779 | 12/1985 | European Pat. Off. | 71/88 |
| 1046429 | 1/1966 | United Kingdom | 71/88 |
| 1175693 | 12/1969 | United Kingdom | 71/94 |
| 1218623 | 1/1971 | United Kingdom | 71/92 |
| 1361816 | 7/1974 | United Kingdom | 71/92 |
| 2134388 | 8/1984 | United Kingdom | 71/92 |

OTHER PUBLICATIONS

Maggie et al, *Pesticide Synthesis Through Rational Approaches*, Eds. American Chemical Society, Washington, DC (1984), pp. 1–82.
O'Brien & Yamamoto, *Biochemical Toxicology of Insecticides*, Academic Press (1970), pp. 21–32.
Summers, *The Bipyridinium Herbicides*, Academic Press (1980), pp. 143–145.
Klingsberg, *Pyridine and Its Derivatives*, Part Two, Erwin Klingsberg (1960), pp. 366–367.
Fieser and Fieser *Advanced Organic Chemistry*, 1961, pp. 341–342 and 673.
Chemical Abstracts, vol. 63, No. 35, Abstract 11422, 1965, Aromatic Compounds, P. Walker et al.
Chem. Abstracts, vol. 63, 11421(h) (1965).
Walker, J. Med. Chem. 8(5), pp. 583–588 (1965).
Chem. Abstracts 61: 8281d (1964).
Hurst, J. et al., J. Chem. Soc. pp. 2948–2955 (1965).
Hickman, J. A. et al., J. Chem. Soc. Perkin Trans. I: 23 pp. 2958–2962 (1972).

*Primary Examiner*—Mary C. Lee
*Assistant Examiner*—Zinna Northington-Davis
*Attorney, Agent, or Firm*—Mervin E. Brokke; Polly E. Ramstad

[57] ABSTRACT 2,3 and 4-(2-cyano-2-arylethyl)pyridines of the formula:

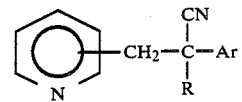

wherein R is a hydrogen, alkyl, cycloalkyl, haloalkyl, alkenyl including dialkenyl, haloalkenyl, akynyl including alkynylalkenyl, alkoxyalkyl, halo(alkoxyalkyl), optionally substituted phenyl, phenylalkyl, phen($c_2$–$C_4$)alkenyl, phenoxyalkyl, a heterocyclic group selected from pyridyl, pyrimidyl, pyrazinyl and furyl or a heterocycloalkyl group wherein the heterocycle is pyridyl, pyrimidyl, pyrazinyl, morpholinyl, pyrrolyl, tetrahydrofuryl, furyl, pyrazolyl or dioxalyl; and Ar is an optionally substituted phenyl or naphthyl group, are new compounds which are fungicidally active, particularly against phytopathogenic fungi.

19 Claims, No Drawings

(2-CYANO-2-ARYLETHYL)PYRIDINE COMPOUNDS USEFUL IN CONTROLLING FUNGICIDAL ACTIVITY

CROSS REFERENCE TO RELATED APPLICATION

This is a continuation of application Ser. No. 888,773, filed July 30, 1986 now abandoned which is a continuation-in-part application of Ser. No. 767,924 filed Aug. 21, 1985 now abandoned.

BACKGROUND OF THE INVENTION

This invention relates to novel compounds which show activity as fungicides, to novel fungicide compositions which contain these compounds and to methods of controlling phytopathogenic fungi.

Several phenyl-pyridyl-alkylnitriles are known. For example, U.S. Pat. No. 3,397,273 is directed toward 3-pyridylmethane derivatives and their use for controlling phytopathogenic fungi. Herbicides which are 2-phenyl-4-cyano-4-(3-pyridyl)butyrate esters or acids are disclosed in U.S. Pat. No. 4,224,052, U.S. Pat. No. 4,313,754 and U.S. Pat. No. 4,383,848. Additionally, phenyl-triazole-alkylnitriles, specifically 1- and 4-aryl-cyanoalkyl-1,2,4-triazoles disclosed in U.S. Pat. No. 4,366,165, are known to have fungicidal activity. However, none of these references teaches the class of compounds of the present invention.

DISCLOSURE OF THE INVENTION

In accordance with the present invention, a new class of 2,3 and 4-(2-cyano-2-phenethyl)pyridines has the formula (I)

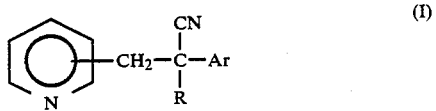

wherein R is a hydrogen, $(C_1-C_8)$alkyl, $(C_3-C_6)$cycloalkyl, halo$(C_1-C_8)$alkyl, $(C_3-C_6)$alkenyl, halo$(C_3-C_6)$alkenyl, $(C_3-C_6)$alkynyl, dialkenyl or alkynylalkenyl having from four to ten carbon atoms, alkoxyalkyl or halo(alkoxyalkyl) having up to a total of eight carbon atoms, tetrahydrofuryl, phenyl, phenyl$(C_1-C_4)$alkyl, phen$(C_2-C_4)$alkenyl, phenoxy$(C_1-C_6)$alkyl, heterocyclic group selected from pyridyl, for example, 4-pyridyl, pyrimidyl, for example, 4- or 5-pyrimidyl, pyrazinyl and furyl, for example, 2-furyl, a heterocyclo$(C_1-C_4)$alkyl group wherein the heterocycle moiety is pyridyl, for example, 4-pyridyl, pyrimidyl, for example, 4- or 5-pyrimidyl, pyrazinyl, morpholinyl, preferably 1-morpholinyl, pyrrolyl, preferably 1-pyrrolyl, pyrazolyl, preferably 1-pyrazolyl, furyl, tetrahydrofuryl or dioxalyl, for example, 2-dioxalyl; and when R is a phenyl, phenylalkyl, phen$(C_2-C_4)$alkenyl or phenoxyalkyl group the phenyl portion may be optionally substituted with up to two substituents selected from halogen, preferably chlorine, bromine or fluorine, nitro, trihalomethyl, preferably trifluoromethyl, cyano, $(C_1-C_4)$alkyl, alkoxyalkyl having up to a total of four carbon atoms, $(C_1-C_4)$alkoxy, $(C_1-C_4)$alkylthio (—Salkyl), $(C_1-C_4)$alkylsulfinyl (—SOalkyl) and $(C_1-C_4)$alkylsulfonyl (—SO$_2$alkyl) groups; and Ar is a phenyl or naphthyl group wherein the phenyl is optionally substituted with up to three, preferably up to two substituents, and wherein the naphthyl is optionally substituted with up to two and preferably up to one substituent. The optional substituents on the phenyl and naphthyl group are each independently selected from halogen, $(C_1-C_4)$alkyl, $(C_1-C_4)$alkoxy, alkoxyalkyl having up to a total of four carbon atoms, nitro, halomethyl, $(C_1-C_4)$-alkylthio (—Salkyl), $(C_1-C_4)$alkylsulfinyl (—SOalkyl), $(C_1-C_4)$alkylsulfonyl (—SO$_2$alkyl) and phenyl which may be substituted with up to one substituent selected from $(C_1-C_4)$alkyl, cyclo$(C_3-C_4)$alkyl, halo$(C_1-C_4)$alkyl, $(C_2-C_4)$alkenyl, $(C_2-C_4)$alkynyl and alkoxyalkyl having up to a total of four carbon atoms; and their acid salts, free bases and metal salt complexes.

When R is a haloalkyl or haloalkenyl, it refers to haloalkyls or haloalkenyls which have up to nine halogens, preferably no more than four halogens and more preferably no more than three halogen atoms. When R is a halo(alkoxyalkyl), it has up to four halogens and preferably no more than two halogen atoms. Moreover, it is preferred that the halogenation of the alkyl, alkenyl or alkoxyalkyl occur near the terminal end of the substituent. Fluorine is the preferred halogen atom when R is a haloalkyl and fluorine or chlorine are preferred when R is a haloalkenyl. When haloalkyl or halomethyl refers to a substituent of the Ar moiety, then it contains no more than three halogens, preferably the halogenation occurs near the terminal end of the haloalkyl and fluorine is the preferred halogen; trifluoromethyl is the more preferred haloalkyl or halomethyl.

The term alkyl as used herein to describe alkyl, haloalkyl, alkoxyalkyl, halo(alkoxyalkyl), phenylalkyl, phenoxyalkyl or heterocycloalkyl includes both straight chained and branched alkyls. The term alkoxyalkyl also includes cyclic alkoxyalkyls, for example, tetrahydrofuryl.

When R is a branched alkyl, it is preferred that the branching not occur at the first carbon of the alkyl, i.e., the carbon attached to the ethyl chain of the 2,3, and 4-(2-cyano-2-arylethyl)pyridines, when R is $(C_1-C_4)$-alkyl or at the first or second carbon of the alkyl when R is $(C_5-C_8)$alkyl.

The 3-(2-cyano-2-phenethyl)pyridines are preferred.

Preferably, R is a $(C_1-C_6)$alkyl, $(C_4-C_6)$alkenyl, $(C_4-C_6)$alkynyl, dialkenyl or alkynylalkenyl having from four to ten carbon atoms, halo$(C_1-C_6)$alkyl, halo$(C_3C_6)$alkenyl, alkoxyalkyl having up to six carbon atoms tetrahydrofuryl, phenyl, phen$(C_1-C_3)$alkyl, phen$(C_2-C_4)$alkenyl or phenoxy$(C_2-C_4)$alkyl wherein the phenyl and phenyl moiety of the phenalkyl, phenalkenyl and phenoxyalkyl groups may be substituted with up to two substituents each independently selected from chlorine, bromine, fluorine, iodine, nitro, trifluoromethyl, cyano, $(C_1-C_4)$alkyl and $(C_1-C_4)$alkoxy groups; and Ar is a phenyl group or a phenyl group substituted with up to two substituents each independently selected from a fluorine, chlorine, bromine, trifluoromethyl, difluoromethyl, monofluoromethyl, $(C_1-C_4)$alkyl, $(C_1-C_4)$alkoxy and phenyl group.

More preferred compounds of the invention are ones wherein R is alkoxyalkyl having up to six carbon atoms including tetrahydrofuryl, $(C_4-C_5)$alkenyl, $(C_3-C_5)$haloalkenyl, dialkenyl or alkynylalkenyl having five to ten carbon atoms, phen$(C_1-C_3)$alkyl, phenoxy$(C_2-C_4)$alkyl or halo$(C_1-C_4)$alkyl having up to three halo atoms, wherein the phenyl portion of the phenalkyl or phenoxyalkyl moiety is optionally substituted with up to two substituents each independently selected from chlorine, bromine, fluorine, trifluoromethyl, cyano, methoxy and ethoxy groups; and Ar is a phenyl group optionally substituted with up to two substituents each independently selected from fluorine, chlorine, bromine, trifluoromethyl, $(C_1-C_2)$alkoxy and phenyl groups.

In a further preferred aspect, Ar is a phenyl group optionally substituted with up to two, preferably optionally up to one, substituents selected from chloro, fluoro, and trifluoromethyl and R is a benzyl or phenethyl group which is optionally substituted with up to one substituent selected from fluoro, chloro, trifluoromethyl, methyl and methoxy In a further aspect, R is a benzyl or benzyl substituted with a fluoro, chloro, trifluoromethyl, methyl or methoxy group.

Typical compounds encompassed by the present invention include:

2-cyano-2-(2,4-dichlorophenyl)-1-(3-pyridyl)hexane,
2-cyano-2-(4-chlorophenyl)-1-(3-pyridyl)heptane,
2-cyano-2-(4-fluorophenyl)-1-(3-pyridyl)hexane,
2-cyano-2-(3-chlorophenyl)-1-(3-pyridyl)pentane,
2-cyano-2-(2-methoxyphenyl)-1-(3-pyridyl)hexane,
2-cyano-2-(3,4-dichlorophenyl)-1-(3-pyridyl)hexane,
2-cyano-2-(2,4-dichlorophenyl)-1-(3-pyridyl)-4-phenyl-hexane
2-cyano-2-(4-chlorophenyl)-5-methyl-(3-pyridyl)hexane,
2-cyano-2-(4-fluorophenyl)-1-(3-pyridyl)hex-5-ene,
2-cyano-2-(3-chlorophenyl)-3-phenyl-1-(3-pyridyl)butane,
2-cyano-2-(2,4-dichlorophenyl)-1-(3-pyridyl)pent-4-yne,
2-cyano-2-(4-chlorophenyl)-4-phenyl-1-(3-pyridyl)butane,
2-cyano-2-(4-fluorophenyl)-2-(2-chlorophenyl)-1-(3-pyridyl)ethane,
2-cyano-2,4-bis(4-chlorophenyl)-1-(3-pyridyl)butane,
2-cyano-2-(2-methoxyphenyl)-3-(4-pyridyl)-1-(3-pyridyl)-propane,
2-cyano-2-(2-nitro-4-chlorophenyl)-1-(3-pyridyl)hexane,
2-cyano-2-(3-trifluoromethylphenyl)-1-(3-pyridyl)hexane,
2-cyano-2-(4-thiomethylphenyl)-1-(3-pyridyl)octane,
2-cyano-2-(2-cyano-4-chlorophenyl)-1-(3-pyridyl)nonane,
2-cyano-2-(4-chlorophenyl)-1-(4-pyridyl)hexane,
2-cyano-2-(4-chlorophenyl)-2-(5-pyrimidyl)-1-(3-pyridyl)-ethane,
2-cyano-2-(2-methoxyphenyl)-1-(4-pyridyl)hexane,
2-cyano-2-(2,4-dichlorophenyl)-1-(2-pyridyl)hexane,
2-cyano-2-(2,4-difluorophenyl)-1-(2-pyridyl)octane,
6-chloro-2-cyano-2-(4-fluorophenyl)-1-(4-pyridyl)-hexane
2-cyano-2-(2,4-dichlorophenyl)-6,6,6-trifluoro-1-(3-pyridyl)hexane,
2-cyano-2-(2,4-dichlorophenyl)-4-phenoxy-1-(3-pyridyl)butane,
2-cyano-2-(2,4-dichlorophenyl)-5-methoxy-1-(3-pyridyl)pentane,
2-cyano-2-(4-phenylphenyl)-1-(3-pyridyl)pentane,
2-cyano-(2-naphthyl)-1-(3-pyridyl)hexane,
2-cyano-2-(4-methylsulfonylphenyl)-1-(3-pyridyl)-hexane,
2-cyano-2-(4-methylsulfinylphenyl)-1-(3-pyridyl)hexane,
2-cyano-2-(3,4-dichlorophenyl)-6-(morpholinyl)-1-(3-pyridyl)hexane,
2-cyano-2-(2,4-difluorophenyl)-5-(4-pyridyl)-1-(3-pyridyl)pentane,
2-cyano-2-(4-chlorophenyl)-2-(3-pyridyl)-1-(3-pyridyl)ethane,
2-cyano-2-(4-chlorophenyl)-2-(5-pyrimidyl)-1-(3-pyridyl)ethane,
2-cyano-2-(4-chlorophenyl)-6-(pyrazolyl)-1-(3-pyridyl)hexane,
2-cyano-2-(4-fluorophenyl)-5-(4-pyrrolyl)-1-(3-pyridyl)pentane,
2-cyano-2-(2,4-dichlorophenyl)-1-(3-pyridyl)propane,
2-cyano-2-(2-chlorophenyl)-1-(3-pyridyl)pentane,
2-cyano-2-(2,4-dichlorophenyl)-3-phenyl-1-(3-pyridyl)propane
2-(4-bromophenyl)-2-cyano-5-fluoro-1-(3-pyridyl)-pentane,
2-cyano-2-(4-chlorophenyl)-5-methoxy-1-(3-pyridyl)-pentane,
2-cyano-2-(4-fluorophenyl)-5-phenoxy-1-(3-pyridyl)-pentane,
2-cyano-2-(4-fluorophenyl)-1-(3-pyridyl)hexane,
2-cyano-2-(4-chlorophenyl)-4-(3-chlorophenyl)-1-(3-pyridyl)butane,
2-cyano-2-(4-chlorophenyl)-1-(3-pyridyl)-5,5-difluorohexane,
2-(4-bromophenyl)-2-cyano-4-(3-fluorophenyl)-1-(3-pyridyl)butane,
2-cyano-2-(2,4-difluorophenyl)-5-methyl-1-(3-pyridyl)hexane,
2-cyano-2-(2,4-dichlorophenyl)-1-(3-pyridyl)pentane
2-cyano-2-(3-fluorophenyl)-3-(4-methoxyphenyl)-1-(3-pyridyl)propane,
2-cyano-2-(3-fluorophenyl)-5-phenyl-1-(3-pyridyl)pen-4ene,
2-cyano-2-(4-chlorophenyl)-5-(3-trifluoromethylphenyl)-1-(3-pyridyl)pentane,
2-cyano-2-(4-chlorophenyl)-6-(4-methylphenyl)-1-(3-pyridyl)hexane,
2-cyano-2-(3,4-dichlorophenyl)-4-phenyl-1-(3-pyridyl)butane,
2-cyano-2-(2,4-difluorophenyl)-4-phenyl-1-(3-pyridyl)butane,
2-cyano-2-(4-chlorophenyl)-4-(2-trifluoromethylphenyl)-1-(3-pyridyl)butane,
2-cyano-2-(4-chlorophenyl)-4(4-methoxyphenyl)-1-(3-pyridyl)butane,
2-cyano-2-(4-chlorophenyl)-6-chloro-5-methoxy-1-(3-pyridyl)hexane and
2-cyano-2-(4-chlorophenyl)-4-(tetrahydrofuryl)-1-(3-pyridyl)butane.

The cyano-aryl-ethylpyridines of the present invention can be prepared by conventional synthetic routes. For example, they may be prepared as shown by Scheme A:

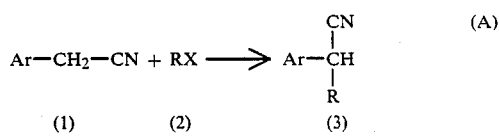

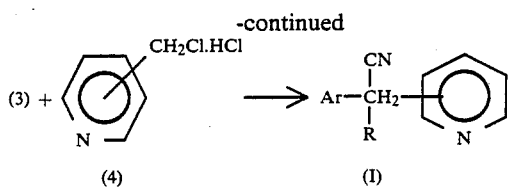

wherein R and Ar are as described previously for Formula (I) except that R is not a phenyl or heterocyclic group and X is a chloride, bromide, methylsulfonate, 4-tolylsulfonate, iodide, benzene sulfonate or another leaving group capable of effecting the desired reaction.

Appropriately substituted arylcyanides (1) are reacted with an organic halide, RX, under basic conditions at a temperature of from about −20° C. to about 50° C., preferably from about −10° C. to about 10° C. Examples of suitable bases include an alkali metal (preferably sodium or potassium) hydroxide and hydride, t-butoxide and dimsyl. Generally the hydroxide bases are used under phase transfer conditions in solvents, such as, methylene chloride, chloroform, carbontetrachloride, benzene, toluene, ethers, tetrahydrofuran (THF) and dioxane. Hydride, t-butoxide and dimsyl bases are used in solvents, for example, toluene, dimethylsulfoxide (DMSO), dimethylformamide (DMF), glyme, ether and THF. The phase transfer conditions usually require catalysts. Suitable catalysts include tetrabutylammonium hydroxide, benzyltriethylammonium chloride or other quaternary ammonium salts, quaternary phosphonium salts and crown ethers, e.g., 18-crown-6. The resulting 2-aryl-1-alkyl-nitrile (3) is preferably purified, e.g., by distillation, and then reacted under basic conditions as described above at a temperature of from about 0° C. to about 50° C. with a salt e.g., hydrochloride salt, of a halomethylpyridine, e.g., chloromethylpyridine (4). The latter may be added as a solid or a solution using as a solvent one (or a mixture) of the solvents described above. The product, a compound of Formula I, may be recovered from the reaction mixture as a free base or as a salt by conventional methods, e.g., adding an appropriate acid to precipitate the desired salt.

If only one reaction vessel is used, then it is preferred that at least three or four equivalents of base to benzyl cyanide (1) are used, that after the organic halide (2) is added, the reaction is allowed to proceed until essentially all of the alkylhalide is consumed before adding the halomethylpyridium salt.

When R is a phenylalkyl or a heterocycloalkyl group as previously described for Formula (I), then the appropriately substituted arylcyanide (1) is reacted with RX where X is a methylsulfonate or a 4-tolylsulfonate under basic conditions created, for example, by sodium or potassium hydride in a solvent such as ether, dioxane, THF, toluene, DMF or DMSO at a temperature of from: about −20 to about 50° C to obtain a 2-aryl-1-alkyl-nitrile (3). The desired cyano-aryl-ethyl-pyridine (I) can then be obtained as described in Scheme A above. The phenylalkyl- and heterocycloalkyl- methylsulfonate or 4-tolylsulfonate can be obtained as shown by Scheme B:

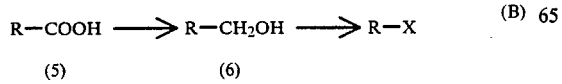

wherein R is phenylalkyl or heterocycloalkyl as described for Formula (I). The organic acid (5) is reduced, for example, with diborane or with lithium aluminum hydride in a solvent such as ether, THF or dioxane to obtain its corresponding alcohol (6). The alcohol (6) is reacted with methanesulfonyl chloride or 4-toluenesulfonyl chloride in the presence of an organic base such as pyridine or triethylamine in a solvent, for example, ether, methylene chloride or chloroform at a temperature of from about −30 to about 10° C.

When R is a cycloalkyl, phenyl, or heterocyclic group, the compounds may be prepared as shown by Scheme C:

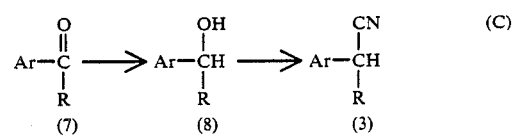

wherein R is a cycloalkyl, phenyl, or heterocyclic group as described previously for Formula (I) and Ar is as described previously for Formula (I).

An appropriately substituted arylketone (7) is reduced to its alcohol (8), for example, by reacting the ketone with sodium borohydride in methanol at reflux or with lithium aluminum hydride in ether at a temperature of from about −20 to about 30° C. The alcohol (8) is then converted to its methylsulfonate or 4-tolylsulfonate, for example, using the process described in Scheme B above. The resulting methylsulfonate or 4-tolylsulfonate is then reacted with sodium or potassium cyanide in a solvent, for example, acetonitrile, DMF or DMSO at a temperature of from about 30 to about 100° C. to obtain a 2-aryl-1-alkylnitrile (3). The pyridine (I) can then be obtained from this nitrile (3) as previously described in Scheme A. Alternatively, when Ar and R are as described previously for Formula (I) except R is not a phenyl or heterocyclic group, the cyano-aryl-ethyl-pyridines can be prepared as shown in Schemes D and E.

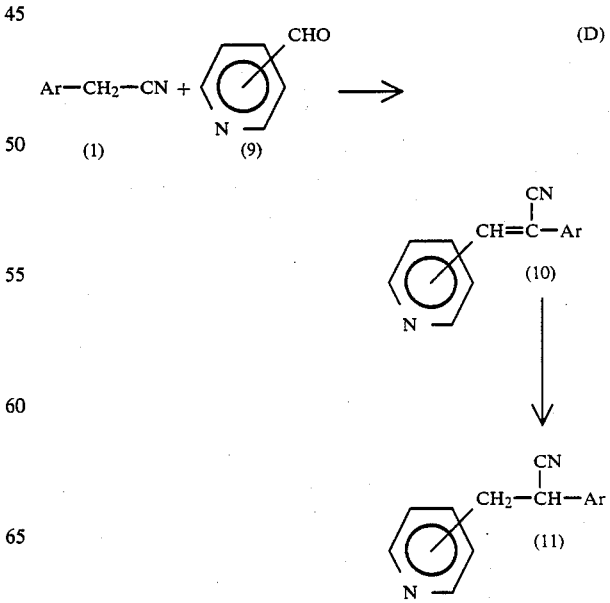

-continued

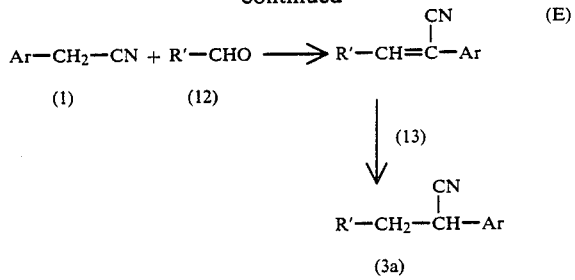

wherein R'—CH$_2$— is a R substituent which is joined to the ethyl chain through a methylene moiety. Scheme E is particularly convenient where R is a benzyl group, i.e., R' is a phenyl group.

According to Scheme D, a suitably substituted arylcyanide (1) is reacted with a pyridinecarboxaldehyde (9) under basic conditions to obtain an intermediate (10) which is subsequently reduced with potassium, lithium or, preferably, sodium borohydride to produce 2-cyano-2-arylpyridylethane (11). The pyridylethane (11) is alkylated with RX (2) under basic conditions to obtain a product of Formula (I). In Scheme E an appropriately substituted arylcyanide (1) is reacted with an aldehyde (12) to obtain an intermediate (13) which is reduced with potassium, lithium or sodium borohydride to obtain compound (3a). Compound (3a) is reacted with a salt of halomethylpyridine, e.g., chloromethylpyridine (4), as described previously for compound (3), to obtain a compound of Formula (I).

The condensation of the arylcyanide (1) with either the pyridinecarboxaldehyde (9) or the aldehyde (12) is conducted in a solvent, for example, an alcohol, ether, DMSO, DMF, toluene, a mixture thereof or water with one or more of these solvents, in the presence of a base at a temperature of from about −10° C. to about 80° C. Preferably, the reaction is performed in an alcohol, i.e., methanol or ethanol, ether or toluene using a catalytic amount of an aqueous base, for example, sodium or potassium hydroxide, at a temperature of from about 0° C. to about 20° C. The intermediate products (10) and (13) are reduced with potassium, or preferably, sodium borohydride in a solvent such as an alcohol, ether or DMF at a temperature of from about 0° C. to about 50° C. Preferably, the reaction is carried out in methanol and at a temperature of from about 5° C. to about 20° C.

The arylcyanides (1), organic halides (2), organic acids (5), organic ketones (8) pyridinecarboxaldehydes (9) and aldehydes (12) can be obtained commercially or prepared by known methods.

The acid salts or metal salt complexes of the (2-cyano-2-arylethyl)pyridines of this invention can be prepared by standard techniques known in the art. For example, the (2-cyano-2-arylethyl)pyridine of formula (I) can be dissolved in an appropriate solvent such as diethylether, tetrahydrofuran, ethanol, methanol, ethylacetate, hexane and toluene or combinations thereof and treated with an equivalent or excess amount of a mineral or organic acid which may or may not be dissolved in an appropriate solvent. The mixture is either cooled or evaporated to get the salt which can either be used as such or recrystallized from an appropriate solvent or combination of appropriate solvents.

The compounds of this invention are useful in the preventative and curative treatment of phytopathogenic fungi, i.e., useful applied either before or after the plant's exposure to a fungus. They are effective against a broad spectrum of fungi, including those of the phycomycetes, ascomycetes, basidiomycetes and deuteromycetes classes. They are particularly effective against powdery mildews, rusts and Rhizoctonia solani (rice sheath blight) and rice blast. Consequently, various compounds of this invention may be useful in treating fungi which may affect cereal crops, fruit crops and vegetable crops.

The pyridines of the invention can be applied as fungicidal sprays by methods commonly employed, such as conventional high-gallonage hydraulic sprays, low-gallonage sprays, air-blast, aerial sprays and dusts. The dilution and rate of application will depend upon the type of equipment employed, the method and frequency of application desired and diseases to be controlled, but the effective amount for application is usually from about 5 grams (gm) to about 22 kilograms (kg), preferably from about 0.010 to about 1.0 kg per hectare.

As a seed protectant, the amount of fungicide coated on the seed is usually at a dosage rate of about 0.0001 to about 10 grams (gm) and preferably from about 0.1 to about 10 gm per 1 kilogram of seed. As a soil fungicide the chemical can be incorporated in the soil or applied to the surface usually at a rate of 0.01 to about 22 kg, preferably about 0.05 to about 11 kg and more preferably from about 0.1 to about 3.3 kg per hectare. As a foliar fungicide the chemical can be applied at a rate of from about 0.01 to about 11 kg, preferably from about 0.02 to about 5.5 kg and more preferably from about 0.1 to about 3.3 kg per hectare.

The present invention is useful for the control of fungi and can be utilized at various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in *McCutcheon's Emulsifiers and Detergents, McCutcheon's Emulsifiers and Detergents/Functional Materials* and *McCutcheon's Functional Materials* all published annually by McCutcheon Division of MC Publishing Company (New Jersey).

In general, the compounds of this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5 to 50% (weight percentage).

For the preparation of emulsifiable concentrates, the compounds used in the invention can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75% (weight percent).

Water based flowable formulations of the compounds can be prepared with a concentration of active ingredients in the range of 5 to 70% by weight, preferably 20 to 50% by weight. A typical flowable formulation is prepared by wet-milling a mixture of 35 parts of 2-cyano-2-(4-chlorophenyl)-4-phenyl-1-(3-pyridyl) butane, 10 parts of Barden clay, 4 parts of sodium lignosulfonate, 1 part of an anionic wetting agent and 50 parts of water.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 5% to 98%, preferably 40% to 75% weight percent). A typical wettable powder is made by blending 50 parts of 2-cyano-2-(4-chlorophenyl)-4-phenyl-1-(3-pyridyl)butane, 45 parts of a synthetic precipitated hydrated silicon dioxide sold under the trademark Hi-Sil®, 1 part of an anionic naphthalenic sulfonate wetting agent and 4 parts of sodium lignosulfonate (Marasperse® N-22). In another preparation of a kaolin type (Barden) clay is used in place of the Hi-Sil in the above wettable powder and in another such preparation 25% of the Hi-Sil is replaced with a synthetic sodium silico aluminate sold under the trademark Zeolex® 7.

Dispersible granule formulations of the compounds can be prepared with a concentration of active ingredients in the range of 5 to 90% by weight, preferably 20 to 75% by weight. A typical dispersible granule is made by blending 50 parts of 2-cyano-2-(4-chlorophenyl)-4-phenyl-1-(3-pyridyl) butane, 20 parts of a synthetic precipitated hydrated silicone dioxide, 20 parts of a kaolin type (Barden clay), 8 parts of sodium lignosulfonate and 2 parts of an anionic wetting agent. The dispersible granule can be prepared by wet agglomeration of the powder mixture with water in a turbulator, powder blender, fluid bed, pan granulator, extruder or the like and then drying and classifying to the desired size.

Dusts are prepared by mixing the amides and salts and complexes thereof with finely divided inert solids which can be organic or inorganic in nature. Materials useful for this purpose include botanical flours, silicas, silicates, carbonates, talc and clays. One convenient method of preparing a dust is to dilute a wettable powder with a finely divided carrier. Dust concentrates containing 20% to 80% (weight percent) of the active ingredient are commonly made and are subsequently diluted to 1% to 10% use concentration.

The compounds of the present invention may also be utilized in combination with other fungicides such as:
(a) dithiocarbamates and derivatives such as:
ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrathiadiazine-2thione (dazomet); and mixtures of these and mixtures with copper salts;
(b) nitrophenol derivatives such as:
dinitro-(1-methylheptyl) phenyl crotonate (dinocap), 2-sec-butyl-4,6-dinitrophenyl-3,3-dimethylacrylate (binapacryl), and 2-sec-butyl-4,6-dinitrophenyl isopropyl carbonate;
(c) heterocyclic structures such as:
N-trichloromethylthiotetrahydrophthalimide (captan), N-trichloromethylthiophthalimide (folpet), 2-heptadecyl-2-imidazole acetate (glyodine), 2-octylisothiazolone-3, 2,4-dichloro-6-(o-chloroanilino)-s-triazine, diethyl phthalimidophosphorothioate, 4-butyl-1,2,4-triazole, 5-amino-1-[bis(dimethylamino)phosphinyl]-3-phenyl-1,2,4-triazole, 5-ethoxy-3-trichloromethyl-1,2,4-thiadiazole, 2,3-dicyano-1,4-dithiaanthraquinone (dithianon), 1,3-dithiolo-[4,5-b]quinoxaline-2-thione (thioquinox), methyl 1-(butylcarbamoyl)-2-benzimidazole carbamate (benomyl), 2-4'-(thiazolyl) benzimidazole (thiabendazole), 4-(2-chlorophenylhydrazono)-3-methyl-5-isoxazolone, 3-(3,5-dichlorophenyl)-5-ethenyl-5-methyl-2,4oxazolidinedione (vinclozolin), 3-(3,5-dichlorophenyl)-N-(1-methylethyl)-2,4-dioxo-1-imidazolidinecarboxamide (iprodione), N-(3,5-dichlorophenyl)-1,2-dimethylcyclopropane-1,2-dicarboximide (procymidone), beta-(4-chlorophenoxy)-alpha-(1,1-dimethylethyl)-1H-1,2,4-triazole-1ethanol (triadimenol), 1-(4-chlorophenoxy)-3,3-dimethyl-1-(1H-1,2,4-triazol-1-yl)-2-butanone (triadimefon), beta-[(1,1'-biphenyl)-4-yloxy]-alpha-(1,1-dimethylethyl)-1H-1,2,4-triazole-1ethanol (bitertanol), 2,3-dichloro-N-(4-fluorophenyl) maleimide (fluoroimide), 1-[2-(2,4-dichlorophenyl)-4-propyl-1,3-dioxolan-2-ylmethyl]-1H-1,2,4-triazole, pyridine-2-thiol-1oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin,alpha-(phenyl)-alpha-(2,4-dichlorophenyl)-5-pyrimidinylmethanol (triarimol), cis-N-[(1,1,2,2-tetrachloroethyl)thio]-4-cyclohexene-1,2-dicarboximide, 3-[2-(3,5-dimethyl-2-oxycyclohexyl)-2-hydroxy]-glutarimide (cycloheximide), dehydroacetic acid, N-(1,1,2,2-tetrachloroethylthio)-3a,4,7,7a-tetrahydrophthalimide (captafol),5-butyl-2-ethylamino-4-hydroxy-6-methyl-pyrimidine (ethirimol), acetate of 4-cyclodecyl-2,6-dimethylmorpholine (dodemorph), and 6-methyl-2-oxo-1,3-dithiolo[4,5-b]-quinoxaline (quinomethionate).
(d) miscellaneous halogenated fungicides such as:
tetrachloro-p-benzoquinone (chloranil), 2-3-dichloro-1,4-napththoquinone (dichlone), 1,4-dichloro-2,5-dimethoxybenzene (chloroneb), 3,5,6-trichloro-o-anisic acid (tricamba), 2,4,5,6-tetrachloroisophthalonitril (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;
(e) fungicidal antibiotics such as:
griseofulvin, kasugamycin and streptomycin;
(f) copper-based fungicides such as:
copper hydroxide, cuprous oxide, basic cupric chloride, basic copper carbonate, copper terphthalate, copper naphthenate and Bordeaux mixture; and
(g) miscellaneous fungicides such as:
diphenyl, sultone, dodecylguanidine acetate (dodine), phenylmercuric acetate, N-ethyl-mercuri-1,2,3,6-tetrahydro-3,6-endomethano- 3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, 1,2-bis(3,-methoxycarbonyl-2-thioureido) benzene (thiophanate-methyl).

EXAMPLES

The following compounds listed in Tables 1 and 2 are meant to be illustrative of the invention.

TABLE 1

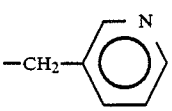

| Compound | Ar | R | Elemental Analysis, Calculated (Found) or NMR (in $CDCl_3$) |
|---|---|---|---|
| 1 | $\phi^1$ | n-butyl | Analysis for $C_{18}H_{20}N_2$: C = 81.81(81.95), H = 7.58(7.70), N = 10.61(10.57). |
| 2 | 2,4-Cl$\phi$ | n-butyl | Analysis for $C_{18}H_{18}N_2Cl_2$: C = 64.86(64.82), H = 5.41(5.40), N = 8.41(7.99), Cl = 21.32(20.29). |
| 3 | 2-OCH$_3\phi^2$ | —CH$_2$-(pyridyl) | 1H-NMR: 8.7–8.3, m, 4H; 7.8–6.8, m, 8H; 4.3, s, 3H; 4.3–3.4, ABq, 4H. |
| 4 | $\phi$ | —CH$_2$-$\phi$ | Analysis for $C_{21}H_{18}N_2$: C = 84.56(81.72), H = 6.04(6.05), N = 9.39(9.26). |
| 5 | $\phi$ | H | Analysis for $C_{14}H_{13}N_2$ ($H_2SO_4$ salt): C = 54.90(52.16), H = 4.58(4.96), N = 9.15(8.65). |
| 6 | $\phi$ | ⊥CH$_2$)$\phi$ | Analysis for $C_{22}H_{20}N_2$: C = 84.87(83.82), H = 6.46(6.34), N = 8.97(9.10). |
| 7 | 4-Cl$\phi$ | n-butyl | 1H-NMR: 8.3–8.2, dd, 1H; 8.1, d, 1H; 7.7–7.1, m, 6H; 3.1, br, 2H; 2.0–1.9, m, 2H; 1.6–0.9, m, 7H. |
| 8 | 4-F$\phi$ | n-butyl | 1H-NMR: 8.3–8.2, dd, 1H; 8.1, br, 1H; 7.6–7.1, m, 6H; 3.2–3.1, ABq, 2H; 3.0–2.0, m, 2H; 1.6–0.8, m, 7H. |
| 9 | 4-Cl$\phi$ | n-propyl | 1H-NMR: 8.3–8.2, dd, 1H; 8.1, br, 1H; 7.4–7.0, m, 6H; 3.3–3.0, ABq, 2H; 2.1–1.9, m, 2H; 1.6–0.9, m, 5H. |
| 10 | 4-F$\phi$ | n-propyl | 1H-NMR: 8.4–8.3, dd, 1H; 8.1, dd, 1H; 7.5–6.9, m, 6H; 3.3–3.0, ABq, 2H; 2.1–1.9, m, 2H; 1.8–0.8, m, 5H. |
| 11 | 2-OCH$_3\phi$ | isopentyl | 1H-NMR: 8.3–8.2, dd, 1H; 8.1, br, 1H; 7.5–6.8, m, 6H; 3.9, s, 3H; 3.6, ABq, 2H; 2.1–1.1, m, 5H; 0.9–0.8, d, 6H. |
| 12 | 4$\phi$-$\phi^3$ | n-butyl | Analysis for $C_{24}H_{24}N_2$: C = 83.49(84.90), H = 7.65(7.46), N = 8.85(8.30). |
| 13[4] | $\phi$ | n-butyl | Analysis for $C_{18}H_{20}N_2$: C = 81.82(81.67), H = 7.58(7.75), N = 10.61(10.59). |
| 14[5] | $\phi$ | n-butyl | Analysis for $C_{18}H_{20}N_2$: C = 81.82(83.02), H = 7.58(7.86), N = 10.61(10.45). |
| 15 | $\phi\phi^6$ | n-propyl | 1H-NMR: 8.5–7.0, m, 11H; 3.4, s, 2H; 2.4–0.8, three m, 7H. |
| 16 | $\phi$ | —(CH$_2$)$_2\phi$(4Cl) | 1H-NMR: 8.5–7.0, m, H; 3.4, s, 2H; 2.7–2.2, ABq, 4H. |
| 17 | $\phi$ | —(CH$_2$)$_3$—O-$\phi$ | 1H-NMR: 8.6–6.8, m, 14H; 3.9, t, 2H; 3.3, s, 2H; 2.5–1.5, m, 4H. |
| 18 | $\phi$ | —CH$_2\phi$(4OMe) | 1H-NMR: 8.5–6.7, m, 12H; 3.7, s, 3H; 3.5, br, 4H. |
| 19 | 3-F$\phi$ | —CH$_2$CH$_2$-$\phi$ | 8.6–8.4, m, 1H; 8.2, m, 1H; 7.5–7.0, m, 11H; 3.42–2.98, ABq, 2H; 3.0–2.2, m, 4H. |
| 20 | 4-Cl$\phi$ | —(CH$_2$)$_4$CH=CH$_2$ | 8.4, m, 1H; 8.0, m, 1H; 7.3–6.95, m, 6H; 5.4–4.7, m, 3H; 3.05, m, 2H; 2.3–1.2, m, 8H. |

TABLE 1-continued

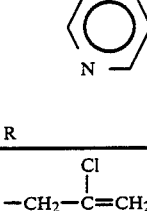

| Compound | Ar | R | Elemental Analysis, Calculated (Found) or NMR (in CDCl$_3$) |
|---|---|---|---|
| 21 | 4-Cl$\phi$ | —CH$_2$—C(Cl)=CH$_2$ | 8.5, m, 1H; 8.0, m, 1H; 7.4–7.0, m, 6H; 5.6–5.0, m, 2H; 3.5–2.9, m, 4H. |
| 22 | 4-Cl$\phi$ | —(CH$_2$)$_3$—C(OCH$_2$CH$_2$O)CH$_3$ | 8.3, m, 1H; 8.0, m, 1H; 7.1, m, 6H; 3.8, s, 4H; 3.2–2.8, ABq, 2H; 2.2–1.2, m, 6H; 1.1, s, 3H. |
| 23 | 2-OEt$\phi$ | n-butyl | 8.4–8.1, two m, 2H; 7.4–6.7, m, 6H; 4.3–3.95, q, 2H; 3.75–3.05, ABq, 2H; 1.6–1.4, t, 3H; 2.0–0.8, m, 9H. |
| 24 | 2-Cl$\phi$ | —(CH$_2$)$_2\phi$(4Cl) | 8.4, m, 1H; 8.3, m, 1H; 7.5–7.0, m, 10H; 3.95–3.25, ABq, 2H; 3.2–2.2, m, 4H. |
| 25 | 4-Cl$\phi$ | —(CH$_2$)$_3$—CH=CH—CH$_3$ | 8.4, m, 1H; 8.05, m, 1H, 7.4–7.0 m, 6H; 5.45–5.3, m, 2H; 3.4–3.0, ABq, 2H; 2.35–1.9, m, 6H; 1.6, d, 3H. |
| 26 | 1-$\phi\phi$[6] | —CH$_2$C(Cl)=CH$_2$ | 8.5, m, 1H; 8.1, m, 1H; 8.0–7.0, m, 9H; 5.4–5.1, m, 2H; 3.9–3.5, m, 4H. |
| 27 | 2-$\phi\phi$[6] | —CH$_2$C(Cl)=CH$_2$ | 8.4, m, 1H; 8.2, m, 1H; 8.0–7.0, m, 9H; 5.4–5.1, m, 2H; 3.5–3.2, m, 4H. |
| 28 | 2-$\phi\phi$[6] | —CH$_2$CH$_2\phi$ | 8.35, m, 1H; 8.15, m, 1H; 7.9–6.9, m, 14H; 3.3–3.1, ABq, 2H; 2.8–2.3, m, 4H. |

[1] $\phi$ is phenyl
[2] —OMe is methoxy
[3] $\phi$-$\phi$ is biphenyl
[4] 4-pyridyl
[5] 2-pyridyl
[6] $\phi\phi$ is naphthyl

TABLE 2

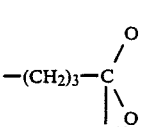

| Compound | X | R | Elemental Analysis, Calculated (Found) or NMR (in CDCl$_3$) |
|---|---|---|---|
| 29 | 4-Cl | —CH$_2$CH=CH$_2$ | 8.4, m, 1H; 7.3–7.0, m, 6H; 5.6–4.9, m, 3H; 3.4–3.0, m, 4H. |
| 30 | 4-Cl | —(CH$_2$)$_3$COCH$_3$ | 8.4, m, 1H, 8.0, m, 1H; 7.4–7.0, m, 6H; 3.4–2.9, ABq, 2H; 2.6–2.35, t, 2H; 2.3–1.8, m, 4H; 2.1, s, 3H. |
| 31 | 3-CF$_3$ | —(CH$_2$)$_2\phi$ | 8.45, m, 1H; 8.1, m, 1H; 7.6–6.9, m, 1H; 3.2, ABq, 2H; 2.8–2.2, m, 4H. |
| 32 | 3-CF$_3$ | —(CH$_2$)$_2\phi$(3-CF$_3$) | 8.5, m, 1H; 8.2, m, 1H; 7.7–7.1, m, 10H; 3.3, ABq, 2H; 3.0–2.4, m, 4H. |
| 33 | 4-Cl | —CH$_2\phi$ | 8.4, m, 1H; 8.05, m, 1H; 7.45–6.9, m, 11H; 3.25, m, 4H. |
| 34 | 4-Cl | —(CH$_2$)$_3$CF$_2$CH$_3$ | 8.5, m, 1H; 8.15, m, 1H; 7.45–7.1, m, 6H; 3.3–3.0, m, 2H; 2.5–1.4, m 9H. |
| 35 | 4-Cl | —CH$_2\phi$(3-OMe) | 8.4, m, 1H; 8.2, m, 1H; 7.4–6.5, m, 10; 3.7, s, 3H; 3.3, m, 2H; 3.4, ABq, 2H. |
| 36 | 4-Cl | —CH$_2$C≡CH | 8.45, m, 1H; 8.2, m, 1H; 7.5–7.0, m, 6H; 3.4–3.0, ABq, 2H; 2.9, d, 2H; 2.2, t, 1H. |
| 37 | 4-Cl | —(CH$_2$)$_3$CF$_3$ | 8.5, m, 1H; 8.2, m, 1H; 7.5–7.1, m, 6H; 3.6–3.1, m, 4H; 2.0–1.8, m, 4H. |
| 38 | H | —CH$_2$C(Me)=CH$_2$ | 8.5, m, 1H; 8.15, m, 1H; 7.5–7.1, m, 6H; 4.9, m, 2H; 3.2, ABq, 2H; 2.8, |

TABLE 2-continued

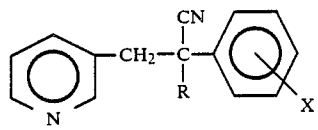

| Compound | X | R | Elemental Analysis, Calculated (Found) or NMR (in CDCl₃) |
|---|---|---|---|
| | | | ABq, 2H; 1.6, s, 3H. |
| 39 | 4-Cl | —CH₂—CH(CH₂)(CH₂) (cyclopropyl) | 8.5, m, 1H; 8.2, m, 1H; 7.5–7.15, m, 6H; 3.95, ABq, 2H; 3.55–3.2, ABq, 4H; 0.6–0.4, m, 2H. |
| 40 | 4-Cl | —CH₂-(2,5-dihydrofuran) | 8.45, m, 1H; 8.2, m, 1H; 7.4–7.0, m, 7H; 6.4, m, 1H; 6.0, m, 1H; 3.4, m, 2H; 3.3, m, 2H. |
| 41 | 3-F | —CH₂C(Cl)=CH₂ | 8.5, m, 1H; 8.2, m, 1H; 7.5–7.0, m, 6H; 5.4–5.2, m, 2H; 3.5–3.1, m, 4H. |
| 42 | 4-F | —CH₂C(Cl)=CH₂ | 8.43, m, 1H; 8.15, m, 1H; 7.5–6.9, m, 6H; 5.4–5.15, m, 2H; 3.5–3.0, m, 4H. |
| 43 | 4-Br | —CH₂C(Cl)=CH₂ | 8.4, m, 1H; 8.2, m, 1H; 7.5–7.0, m, 6H; 5.4–5.15, m, 2H; 3.5–3.0, m, 4H. |
| 44 | 4-Cl | —CH₂φ(3-F) | 8.5, m, 1H; 8.2, m, 1H; 7.5–7.1, m, 7H; 7.0–6.7, m, 3H; 3.4–3.2, m, 4H. |
| 45 | 4-F | —(CH₂)₂φ | 8.5, m, 1H; 8.2, m, 1H; 7.5–7.0, m, 11H; 3.2, ABq, 2H; 3.0–2.3, m, 4H. |
| 46 | 3,4-diCl | —(CH₂)₂φ | 8.5, m, 1H; 8.2, m, 1H; 7.5–7.0, m, 10H; 3.1, m, 2H; 3.0–2.3, m, 4H. |
| 47 | 4-Cl | —(CH₂)₂φ | 8.5, m, 1H; 8.2, m, 1H; 7.4–7.0, m, 11H; 3.2, m, 2H; 3.0–2.3, m, 4H. |
| 48 | H | —CH₂C(Cl)=CH₂ | 8.45, m, 1H; 8.1, m, 1H; 7.5–7.05, m, 7H; 5.4–5.2, m, 2H; 3.5–3.0, m, 4H. |
| 49 | 4-Br | —(CH₂)₂φ | 8.5, m, 1H; 8.2, m, 1H; 7.5–7.0, m, 11H; 3.3–3.1, ABq, 2H; 2.8–2.2, m, 4H. |
| 50 | 4-Cl | —(CH₂)₂CH=CH₂ | 8.5, m, 1H; 8.2, m, 1H; 7.45–7.1, m, 6H; 5.8, m, 1H; 5.0, m, 2H; 3.35–3.1, ABq, 2H; 2.35–1.85, m, 4H |
| 51 | 4-Cl | —CH₂CH=CHC≡C—CMe₃ | 8.4, m, 1H; 8.0, m, 1H; 7.4–6.95, m, 6H; 5.8–5.4, m, 2H; 3.3–2.7, m, 4H; 1.2, s, 9H. |
| 52 | 4-Cl | —CH₂CH=CHφ | 8.4, m, 1H; 8.1, m, 1H; 7.2, m, 11H; 6.5–5.8, m, 2H; 3.2, ABq, 2H; 2.9, d, 2H. |
| 53 | 3,4-diCl | —CH₂C(Me)=CH₂ | 8.5, m, 1H; 8.2, m, 1H; 7.6–7.0, m, 5H; 4.9, m, 2H; 3.2, ABq, 2H; 2.9, m, 2H; 1.7, s, 3H. |
| 54 | 3-CF₃ | —CH₂C(Cl)=CH₂ | 8.45, m, 1H; 8.2, m, 1H; 7.7–7.15, m, 6H; 5.4–5.2, m, 2H; 3.5–3.1, m, 4H. |
| 55 | 3,4-diCl | —CH₂C(Cl)=CH₂ | 8.5, m, 1H; 8.2, m, 1H; 7.5–7.4, m, 3H; 7.3–7.1, m, 2H; 5.4–5.1, m, 2H; 3.6–3.0, m, 4H. |
| 56 | 2,4-diF | —CH₂C(Cl)=CH₂ | 8.5, m, 1H; 8.2, m, 1H; 7.6–7.2, m, 3H; 7.0–6.7, m, 3H; 5.4–5.1, m, 2H; 3.6–3.1, m, 4H. |
| 57 | 4-Cl | —(CH₂)₂φ(4-OMe) | 8.47, m, 1H; 8.15, m, 1H; 7.4–6.75, m, 10H; 3.75, s, 3H; 3.3–3.05, ABq, 2H; 2.75–2.25, m, 4H. |
| 58 | 4-Cl | —(CH₂)₂Oφ | 8.5, m, 1H; 8.15, m, 1H; 7.4–6.7, m, 11H; 4.2–3.75, m, 2H; 3.4–3.1, ABq, 2H; 2.55, m, 2H. |
| 59 | 3-F | —(CH₂)₂φ(4-OMe) | 8.45, m, 1H; 8.15, m, 1H; 7.4–6.8, m, 10H; 3.75, s, 3H; 3.3–3.1, ABq, 2H; 2.85–2.25, m, 4H. |
| 60 | 3-F | —(CH₂)₂Oφ | 8.45, m, 1H; 8.15, m, 1H; 7.4–6.7, m, 11H; 4.2–3.8, m, 2H; 3.3–3.05, ABq, 2H; 2.55, m, 2H. |
| 61 | 4-Cl | —(CH₂)₃Oφ | 8.5, m, 1H; 8.15, m, 1H; 7.4–6.8, m, 11H; 3.9, t, 2H; 3.3–3.05, ABq, 2H; 2.4–1.6, m, 4H. |
| 62 | 4-Cl | —(CH₂)₂φ(2-CF₃) | 8.5, m, 1H; 8.15, m, 1H; 7.6–7.1, m, 10H; 3.4–3.1, ABq, 2H; 3.0–2.3, m, 4H. |
| 63 | 4-Cl | —(CH₂)φ(4-CN) | 8.45, m, 1H; 8.2, m, 1H; 7.5–7.1, m, 10H; 3.45–3.25, m, 4H. |
| 64 | 4-Cl | —CH₂φ(4-tBu) | 8.45, m, 1H; 8.2, m, 1H; 7.4–7.0, m, |

TABLE 2-continued

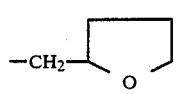

| Compound | X | R | Elemental Analysis, Calculated (Found) or NMR (in CDCl₃) |
|---|---|---|---|
| 65 | 4-Cl | —(CH₂)₄OMe | 10H; 3.4–3.2, m, 4H; 1.3, s, 9H.<br>8.45, m, 1H; 8.1, m, 1H; 7.4–7.1, m, 6H; 3.3, s, 3H; 3.3–3.0, m, 4H; 2.2–1.2, m, 6H. |
| 66 | 4-Cl | —(CH₂)₄Oφ | 8.45, m, 1H; 8.15, m, 1H; 7.4–6.8, m, 11H; 3.9, m, 2H; 3.3–3.0, ABq, 2H; 2.2–1.2, m, 6H. |
| 67 | 4-Cl | CH₂φ(3-CF₃) | 8.5, m, 1H; 8.25, m, 1H; 7.6–7.1, m, 10H; 3.6–3.4, m, 4H. |
| 68 | 4-Cl | —CH₂φ(4-Me) | 8.5, m, 1H; 8.2, m, 1H; 7.5–6.9, m, 10H; 3.4–3.2, m, 4H; 2.3, s, 3H. |
| 69 | 4-Cl | —CH₂-(tetrahydrofuranyl) | 8.45, m, 1H; 8.15, m, 1H; 7.5–7.1, m, 6H; 4.3–3.8, m, 4H; 3.55–3.2, ABq and m, 3H; 2.2–1.7, m, 3H. |
| 70 | 2,4-diF | —(CH₂)₂φ | 8.5, m, 1H; 8.25, m, 1H; 7.5–6.7, m, 10H; 3.5–3.25, ABq, 2H; 2.9–2.2, m, 4H. |

EXAMPLE 2

2-Cyano-2-(2,4-dichlorophenyl)-1-(3-pyridyl) hexane

In a three-neck round-bottom flask equipped with a stirrer, a thermometer, an addition funnel and a reflux condenser was placed 3-chloromethylpyridine hydrochloride (4.9 gm, 0.03 mole), 2-(2,4-dichlorophenyl)hexane nitrile (7.26 gm, 0.03 mole), benzyltriethylammonium chloride (2 gm) and hexane (50 ml). Aqueous 50% sodium hydroxide (80 ml) was added with rapid mixing at such a rate that the temperature remained below about 30° C. After stirring for about 2 hours at 25°–30° C., the reaction mixture was diluted with ice water and extracted with methylene chloride. The organic extractant was washed with water and brine, dried over magnesium sulfate and the solvent removed. A clear yellow oil was obtained of the pure product (9 gm).

Examples 1, 4–5, 13, 14, 19–22, 24 and 25 were prepared in a similar manner and instead of 2-(2,4-dichlorophenyl)hexane nitrile using: 2-phenylhexane nitrile, 2,3-diphenylpropionitrile, 2-(3-fluorophenyl)-4-phenylbutyro nitrile, 2-(4-chlorophenyl)-2-hexen-5-yl nitrile, 2-(4-chlorophenyl)-7-octenyl nitrile, 2-(4-chlorophenyl)4-chloro-4-pentene nitrile and 2-(2-chlorophenyl)-4-(4chlorophenyl)butyro nitrile.

EXAMPLE 10

2-Cyano-2-(4-fluorophenyl)-b 1-(3-pyridyl) pentane (a) To a reaction flask was added 400 gm (2.96 moles) of p-fluorophenylacetonitrile, 465 gm (5.92 moles) of 1-chloro-propane and 9.07 gm (0.3 mole) of tetrabutylammonium bromide. Then 592 gm (7.4 moles) of 50% (w/w) sodium hydroxide was added over 2.5 hours to the reaction flask with the reaction temperature rising to about 35° C. Thereafter, the reaction mixture was heated to about 45° C. and stirred for about 12 hours. Upon completion, the reaction was quenched with water and the mixture extracted three times with ether, then rinsed three times with water followed by a brine rinse. It was then distilled to yield 358.8 gm of 91% pure 2-cyano-2-(4-fluorophenyl)butane.

(b) A three-neck 300 ml round-bottom flask was equipped with a thermometer, an addition funnel, a reflux condenser and a magnetic stirring bar. Sodium hydride (6 gm of 60% NaH, 0.15 mole) was placed in the flask under a nitrogen atmosphere, washed with hexane (3×25 ml), and then a solution of 2-cyano-2-(4-fluorophenyl)butane (13.3 gm, 0.075 mole) in DMF (10 ml) was added. This slurry was cooled to about −10° C., then 3-chloromethylpyridine (12.3 gm, 0.075 mole) was added in portions over 15 minutes and an exothermic reaction was observed. The mixture was stirred at room temperature for about 3 hours, thereafter water (25 ml) was added gradually at 0° C. The reaction mixture was transferred to a separatory funnel using ether (300 ml) as a rinse. The resulting mixture was washed with water (2×50 ml). The organic layer was dried over magnesium sulfate and the solvent removed to obtain a yellow oil which crystallized slowly to yield 16.1 gm of the desired product.

Examples 3, 6–9, 11–12, 15, 17–18 and 23 were prepared in a similar manner, using the appropriately substituted arylacetonitrile and instead of 1-chlorobutane using 1-chloro-2-phenylethane, 1-chloropropane, 1-chloro3-methylbutane, 1-chloro-3-phenoxypropane and alpha-chloro-4-methoxytoluene.

EXAMPLE 16

4-(4-Chlorophenyl)-2-cyano-2-phenyl-1-(3-pyridyl)butane (a) To a reaction vessel under a nitrogen atmosphere was added 38 gm sodium hydride (0.95 mole), washed with hexane, in about 1600 ml of dry toluene and DMF (2:1) and then cooled in an ice-water bath. Benzylcyanide (117.5 gm, 1 mole) was added gradually over about 1.5 hours, and the mixture then stirred for another about 3.5 hours until the evolution of hydrogen ceased Then, 223 gm of 4-chlorophenethylmethanesulfonate (0.95 mole) in about 350 ml of toluene and DMF (2:1) was added over about 6 hours, and the mixture stirred overnight at room temperature. About 3000 ml of water was then added and the slurry transferred to a separatory funnel and extracted with ether. The combined ether extracts were washed sequentially with water, 5% hydrochloric acid, water and brine. After drying and removal of solvent, 230 gm of product were obtained which was distilled to recover 145 gm of 3-(4-chlorophenyl)-1-cyano-1-phenylpropane.

This product was also obtained by charging a reaction vessel with 58.6 gm of benzylcyanide (0.5 mole), 116.8 gm of 4-chlorophenethylmethanesulfonate (0.5 mole), 500 ml of toluene and 500 ml of dimethylsulfoxide. The mixture was cooled to about 5° C. and 50% sodium hydroxide was added slowly with rapid mixing while maintaining the temperature at about 5°-10° C. After the addition of the sodium hydroxide (about 1.5 hours), the mixture was allowed to warm to room temperature and then stirred for another three hours. One liter of water was added to the mixture and it was transferred to a separatory funnel where it was extracted with ether; the combined ether extracts were sequentially washed with 5% hydrochloric acid, water and brine. The liquid obtained after solvent removal was distilled to obtain 102 gm of 3-(4-chlorophenyl)-1-cyano1-phenylpropane.

(b) To a reaction vessel was added 3.2 gm sodium hydride (60% NaH, 0.078 mole) which was washed with hexane. This sodium hydride was slurried in DMF under a nitrogen atmosphere, then to it was added gradually 5.0 gm of 3-(4-chlorophenyl)-1-cyano-1-phenylpropane (0.0196 mole). This reaction mixture was cooled to about 0°-5° C. and 3.2 gm of picolylchloride hydrochloride (0.0196 mole) was added in small portions After complete addition, the reaction was stirred for about one hour while maintaining the temperature at about 0°-5° C., then it was allowed to warm to room temperature and stirred for another about 3 hours. The reaction was then quenched with water and the mixture transferred to a separatory funnel, using ether as a wash. The combined ether layers were washed with water and brine, dried over magnesium sulfate and concentrated on a rotary evaporator. Purification of the product by chromatography over silica gel resulted in 3.5 gm of 4-(chlorophenyl)-2-cyano-2-phenyl-1-(3-pyridyl) butane.

EXAMPLES 26-70

Preparation of
1-Cyano-1-(4-Chlorophenyl)-2-(3-Pyridyl)Ethane

In a 3-liter four neck flask equipped with mechanical stirrer, a thermometer and an addition funnel was placed 4-chlorobenzyl cyanide (110.0 gms, 0.738 m), methanol (800 ml), 3-pyridinecarboxaldehyde (81.0 gms, 0.74 m). This mixture was cooled to 10° C using an ice water bath. Aqueous sodium hydroxide (40 ml of 10% solution) was added to the flask gradually with stirring over 15 minutes. A precipitate started to appear shortly after the addition of sodium hydroxide. The stirring was continued for an hour at 10° C. and for another hour at room temperature. Water (500 ml) was then added to facilitate the precipitation of alpha-(4-chlorophenyl)-beta-(3-pyridyl)acrylonitrile, which was isolated by filtration. After drying, 157 gms of this product was obtained.

The acrylonitrile (80 gms, 0.3 m) was added to methanol (1200 ml) in a 2-liter flask equipped with magnetic stirrer and a cooling bath. The reaction flask was kept under nitrogen atmosphere and sodium borohydride (14 gms, 0.36 m) was added in portions with stirring while keeping the reaction temperature below about 30° C. After complete addition of the sodium borohydride, the cooling bath was removed and the mixture was stirred for 12 hours at room temperature. Most of the methanol was removed by evaporation and the product was allowed to crystallize from the residue. The solid was filtered and washed with water and methanol, then dried. Sixty-four grams of the titled compound was obtained.

This product was used to make the compounds 29, 30, 33-37, 39, 40, 44, 47, 50, 52, 57, 58 and 61-69. 1-cyano1-aryl-2-(3-pyridyl)ethane used to make compounds 26-28, 31, 32, 38, 41-43, 45, 45, 48, 49, 53-56, and 59-60 was prepared in a similar manner using an appropriately substituted arylcyanide instead of 4-chlorobenzyl cyanide, e.g., 1- and 2-naphthylacetonitrile, 3-trifluoromethylbenzyl cyanide, benzyl cyanide, 3-, 4- and 2,4- fluorobenzyl cyanide, 4-bromobenzyl cyanide and 3,4-dichlorobenzyl cyanide.

EXAMPLE 30

2-Cyano-2-(4-Chlorophenyl)-1-(3-Pyridyl)Heptan-6-One

2-Cyano-2-(4-chlorophenyl)-1-(3-pyridyl)heptan-6-one ketal (18.5 gm, 0.05 m) and ethyl acetate (200 ml) were placed in a 500 ml flask and cooled to about 5° C. (the ketal was prepared in a manner similar to that described for compound 36 below except instead of propargyl bromide using 2-(3-bromopropyl)-2-methyl-1,3-dioxolane). Ice cold sulfuric acid (40 ml of concentrated sulfuric acid in 40 gm of ice) was added to the flask while stirring. The mixture was allowed to warm to room temperature and after about ½ hour, the two phase mixture was poured into saturated sodium carbonate (500 ml) with mixing. The product was extracted with ether (3×200 ml), the organic layer was washed with water then brine, and dried. Removal of the solvent yielded 15.5 gm of compound 30.

EXAMPLE 34

2-Cyano-2-(4-Chlorophenyl)-6,6-Difluoro-1-(3-Pyridyl)Heptane

2-Cyano-2-(4-chlorophenyl)-1(3-pyridyl)heptane-6-one (2.0 gm, 0.006 m) was added to methylene chloride (50 ml) under a nitrogen atmosphere. Diethylammonium sulfur tetrafluoride (DAST 10 gm) was added gradually with stirring at room temperature. The mixture was stirred for about 12 hours. The reaction flask was placed in an ice water bath and the reaction was quenched by adding water. Methylene chloride (200 ml) was added, the resulting organic layer was separated and washed with water (3×50 ml) then brine (50 ml) and dried. After solvent removal, the residue was purified using flash chromatography to obtain 1.8 gm of compound 34.

EXAMPLE 36

2-Cyano-2-(4-chlorophenyl)-1-(3-Pyridyl)-pent-5-yne

1-Cyano-1-(4-chlorophenyl)-2-(3-pyridyl)ethane (4.85 gms, 0.02 m) was placed in a 500 ml three neck flask equipped with a mechanical stirrer, addition funnel and a cooling bath. Propargyl bromide (6 ml), methylene chloride (200 ml) and benzyltriethylammonium chloride (1.0 gm) were added to the flask and the mixture was cooled to about 10° C. Then 50% sodium hydroxide (20 ml) was added dropwise while keeping the reaction temperature between about 10°–20° C. The mixture was stirred at room temperature for 1 hour. Contents of the reaction vessel were transferred to a separatory funnel using methylene chloride (100 ml) and water (100 ml) to rinse the vessel. The methylene chloride layer was washed with water (2×100 ml) and brine (100 ml), dried and the solvent removed. The residue was chromatographed over silica gel to obtain 2.7 gms of the product.

Compounds 22, 26, 27, 29, 33, 35–44, 48, 50–56, 63, 64, 65 and 67–69 were prepared in a similar manner using the appropriately substituted 1-aryl-1-cyano-2-(3-pyridyl)ethane and instead of propargyl bromide using: 2-(3-bromo-propyl)-2-methyl-1,3-dioxolane, 2-propenyl bromide, benzyl bromide, 3-methoxybenzyl bromide, 4-trifluorobutyl bromide, 2-chloropropen-2-yl bromide, cyclopropanemethyl bromide, 2-furylmethyl bromide, 3-fluorobenzyl bromide, 3-butenyl bromide, 1-bromo-6,6-dimethylhept-2-ene-4-yne, cinnamyl bromide, 2-methylpropen-2-yl bromide, 4-cyanobenzyl bromide, 4-t-butylbenzyl bromide, 3-trifluoromethylbenzyl bromide, 4-methylbenzyl bromide and 2-tetrahydrofurylmethyl bromide.

EXAMPLE 57

2-Cyano-2-(4-Chlorophenyl)-4-(4-methoxyphenyl)-1-(3-pyridyl)butane

1-Cyano-1-(4-chlorophenyl)-2-(3-pyridyl)ethane (4.0 gms, 0.0165 m) was placed in a 100 ml three neck flask, under a nitrogen atmosphere, equipped with a magnetic stirrer, thermometer, gas inlet tube and a cooling bath. To the flask was added 50 ml DMF-toluene (1:2), and the resulting solution was cooled to 5° C. Sodium hydride (0.4 gm, 0.018m of 60% NaH) was added and the mixture was stirred for 30 minutes. Then 4-methoxyphenyl-p-toluene-sulfonate (5.0 gm, 0.0165 m) was added and the mixture was stirred for 1 hour at 5° C., followed by stirring at room temperature for another 2 hours. The reaction mixture was quenched with water (10 ml), then placed in a separatory funnel using methylene chloride (200 ml) as a rinse. The organic layer of methylene chloride was washed with water (5×100 ml) and brine (100 ml), then dried. Solvent removal followed by column chromatographic purification afforded 3.6 gms of the titled compound.

Compounds 31, 32, 45–47, 49, 58, 60, 61, 62, 65, 66 and 70 were prepared in a similar manner using the appropriately substituted 1-phenyl-1-cyano-2-(3-pyridyl)-ethane and instead of 4-methoxyphenethyl-p-toluenesulfonate using: phenethyl bromide, 3-trifluoromethylphenethyl-p-toluenesulfonate, phenoxyethyl chloride, phenoxypropyl chloride, 2-trifluoromethylphenethyl-ptoluenesulfonate, methoxybutyl chloride and phenoxybutylchloride.

EXAMPLE 70

The compounds of Examples 1–70 were tested (not necessarily at the same time) for their fungicidal activity in vivo against wheat powdery mildew (WPM), wheat stem rust (WSR), wheat leaf rust (WLR), barley Helminthosporium (BH), rice blast (RB), rice sheath blight (RSB), peanut Cercospora (PC), bean Botrytis (BOT), cucumber downy mildew (CDM), tomato late blight (TLB) and grape downy mildew (GDM). In tests of compounds 1–18 on cereals, the plants were trimmed about 24 hours prior to the application of the fungicide compound to provide a uniform plant height and to facilitate uniform application of the compound and inoculation with the fungus. Compounds 1–18 were dissolved in a 2:1:1 mixture of water, acetone and methanol, sprayed onto the plants, allowed to dry (four to six hours) and then the plants were inoculated with the fungus. Compounds 19–70 were dissolved in a 1:1 mixture of acetone and methanol, sprayed onto the plants and allowed to dry for about 24 hours before inoculating with the fungus. Each test utilized control plants which were sprayed with the solvent mixture and inoculated with the fungus. The remainder of the technique of each of the tests is given below and the results are reported in Tables 3 and 4 as percent disease control (percentages of plants treated with the compounds of the present invention lacking disease sign or symptoms compared to the untreated control plants).

A. Wheat Powdery Mildew (WPM)

*Erysiphe graminis* (f. sp. *tritici*) was cultured on Pennol or wheat seedlings in a controlled temperature room at 65° to 70° F. Mildew spores were shaken from the culture plants onto Pennol or Hart wheat seedlings which had been previously sprayed with the fungicide compound. The inoculated seedlings were kept in a controlled temperature room at 65° to 75° F. and subirrigated. The percent disease control was rated 8 to 10 days after the inoculation.

B. Wheat Stem Rust (WSR)

*Puccinia graminis* (f. sp. tritici Race 15B-2) was cultured on Wanzer or Tyler wheat seedlings for a period of 14 days in a greenhouse. For compounds 1–18 a water suspension of the spores from infested plants was obtained and the spore concentration was adjusted to about $2 \times 10^5$ spores per ml of deionized water. The wheat plants which had been previously treated with the fungicide compounds were inoculated by applying the stem rust spore suspension, until runoff, with a DeVilbiss atomizer at 5 lbs. per square inch air pressure. For compounds 19–70 an oil suspension of the spores was prepared which had about $4 \times 10^5$ spores per milliliter of oil. The inoculum was dispensed in gelatin capsules and applied with a vacuum pump by making 4 passes on both sides of the wheat plants. After inoculation, the plants were placed in a humid environment at approximately 75° F. where they were exposed to 12 hours of continuous darkness followed by a minimum of 3 to 4 hours of light having an intensity of about 500 footcandles. The temperature in the chamber did not exceed 85° F. At the end of the light period, the plants were placed in a greenhouse where they were permitted to grow for a period of about two weeks at which time the percent disease control was determined.

C. Barley Helminthosporium (BH)

*Helminthosporium sativum* was cultured on Pennrad barley plants. A water suspension of the spores from infested plants was obtained and the spore concentration was adjusted to about $2 \times 10^5$ spores per ml of deionized water. Other Pennrad barley plants which had been sprayed with the fungicide compounds were inoculated with this fungus by spraying the foliage of the plants with a hand sprayer until small droplets of the inoculum were observed on the leaves. The inoculated plants were incubated in a humid environment at a temperature of from 75° to 85° F. for 24 hours, then

D. Rice Blast (RB)

Untrimmed Nato or cultivar M-201 rice plants were inoculated with *Piricularia oryzae* (about 20,000-30,000 conidia per ml) by spraying the leaves and stems until a uniform film of inoculum was observed on the leaves. The inoculated plants were incubated in a humid environment (75° to 85° F.) for 24 or 48 hours, then placed in a greenhouse environment (70° to 75° F.). Seven to eight days after inoculation, the percent disease control was determined.

The inoculum was produced on plates of oatmeal agar containing 50 gm of Gerber grand baby oatmeal, 20 gm of bacto agar, 10 gm bacto dextrose and 1000 ml deionized water. The plates were inoculated with mycelial plugs (7-14 days old) *Piricularia oryzae* and maintained at room temperature under constant fluorescent light for 10-14 days. The plates were then flooded with a solution of 0.25 gm sodium oleate, 2 gm gelatin and 1000 ml deionized water and the plates scraped to release condia. The resulting mixture was filtered through cheesecloth and the spore suspension adjusted using a hemacytometer.

E. Rice Sheath Blight (RSB)

*Pellicularia filamentosa* f. sp. *sasiki* was cultured on an autoclaved mixture of crushed rice seeds and potato dextrose broth (100 gms of rice seeds per 30 ml of potato dextrose broth) in a 500 ml Erlenmeyer flask. After ten days, the culture was blended in a blender to produce a uniform inoculum. For a portion of the tests, the inoculum was prepared by shake culturing a small piece of mycelium or a single sclerotium of the same organism in 500 ml Erlenmeyer flasks containing 150 ml of potato dextrose broth at 22° C with photoperiods of 14-16 hours. After six days, 23 gm of mycelium (wet weight) was blended with 100 ml of deionized water and 20 gm of rice flour to produce a uniform inoculum. Approximately one teaspoon of inoculum was spread among Lebonnet or M-201 rice seedlings on the soil surface of each pot of seedlings. The inoculated seedlings were incubated for five days in a humidity cabinet (85° to 90° F.). Percent disease controls were determined by comparing the height of mycelial growth observed to that of the control plants, immediately after removing the seedlings from the cabinet.

F. Peanut Cercospora (PC)

*Cercospora arachidicola* was cultured on peanut and oatmeal agar (POA) in petri dishes for 14 days under fluorescent lights that were about 20 cm above the cultures. The petri dishes were inoculated with 0.5 ml of a concentrated spore suspension in sterile water containing a few drops of polysorbate 80 (Tween 80). The spore suspension was subsequently spread over the surface of the POA plates by means of a sterile, bent glass rod. Spores were harvested from plates by adding deionized water containing a small amount of polysorbate 80 (Tween 80) to the POA plates. The agar surface was scraped to obtain a spore suspension which was filtered through cheesecloth and then adjusted to a concentration of 2 to $4 \times 10^5$ spores per ml of water.

Tamnut 74 peanut plants which had been previously treated with the fungicide compounds were inoculated by spraying the leaves with inoculum until a uniform film was observed on the plants. The inoculated plants were incubated in a humid environment at 85° to 90° F for 72 hours. They were removed from the humid environment, allowed to dry and placed in a greenhouse. The percent disease control was determined 10 to 14 days after inoculation.

G. Bean Botrytis (BOT)

*Botrytis fabae* was cultured on potato dextrose agar in petri dishes for 14 days at room temperature in the dark. The petri dishes were flooded with a mix of water and apple juice (2:1 by volume) and the conidia were scraped off the culture surface into the liquid. Three week old *Vicia faba* (English Broad Bean) plants which had been previously treated with the fungicide compounds were misted with the conidial suspension. The treated and inoculated plants were kept in a mist chamber at about 70° F. under low light for about 3 days after which the percent disease control was determined.

H. Cucumber Downy Mildew (CDM)

*Pseudoperonospora cubensis* was maintained on leaves of live Marketer cucumber plants in a constant temperature room at 65° to 75° F. in humid air with moderate light intensity for 7 to 8 days. A water suspension of the spores from infested leaves was obtained and the spore concentration was adjusted to about $1 \times 10^5$ per ml of water.

Marketer cucumber seedlings were inoculated by spraying the underside of the leaves with a DeVilbiss atomizer until small droplets were observed on the leaves. The inoculated plants were incubated in a mist chamber for 24 hours at about 70° F. and then subsequently incubated for 6 to 7 days in a controlled temperature room under mist at 65° to 75° F. Seven days after inoculation, the percent disease control was determined.

I. Tomato Late Blight (TLB)

*Phytophthora infestans* was maintained on 6 to 8 inch tall Rutgers or Pixie tomato seedlings for 4 to 5 days in a constant temperature humidity chamber at 65° to 75° F. with moderate light intensity. A water suspension of the spores from infested plants was obtained and the spore concentration was adjusted to about $1 \times 10^5$ spores per ml of water. The spore suspension was applied to the lower leaf surfaces of Rutgers or Pixie tomato seedlings (which had been previously treated with the chemical compounds) with a DeVilbiss atomizer until fine droplets were visible on the leaves. The inoculated seedlings were placed in a humidity cabinet at 65° to 70° F. for 24 hours and then moved to a high humidity controlled temperature chamber until treatment evaluations were made 4 to 7 days after inoculation.

J. Grape Downy Mildew (GDM)

*Plasmopora viticola* inoculum was prepared by washing conidia from sporulating leaves of DeChaunac grape plants. The spore suspension was standardized to a concentration of about $4 \times 10^5$ spores per ml of water and hand sprayed onto the underside of the leaves of DeChaunac grape plants which had been previously treated with the fungicide compounds. The plants were incubated for 24 hours in a humidity cabinet at about 20° C and subsequently moved to a constant temperature room at about 68° F and 1000 footcandles of light on a 12 hour cycle. After 6 days, the plants were placed in a mist chamber for 24 hours at about 68° F. after which sporulation was apparent on the underside of the leaves. Treatment evaluations were then made.

K. Wheat Leaf Rust (WLR)

*Puccinia gramini* (f. sp. *recondita*) was cultured on Fielder wheat seedlings for 2–3 weeks. Spores were harvested from these infected plants and added to light mineral oil at a concentration of $4 \times 10^5$ spores per milliliter of oil. The inoculum was dispersed in gelatin capsules and applied with a vacuum pump to 7-day old Fielder wheat seedlings by making four passes on both sides of the seedlings. After about 20 minutes the plants were placed in a 100% humidity cabinet at a temperature of 70° F. overnight. Then the plants were transferred to a greenhouse and evaluated thirteen days later.

TABLE 3

| Compound (300 ppm) | Percent Disease Control | | | | | | | | | |
|---|---|---|---|---|---|---|---|---|---|---|
| | WPM | WSR | BH | RB | RSB | PC | BOT | CDM | TLB | GDM |
| 1 | 100(3) | 90 | 100 | 60(2) | 0 | 100 | 45 | 70 | 0 | — |
| 2 | 100(2) | 30(2) | 99 | 45(3) | 0 | 95(2) | 0 | 63(3) | 95(2) | 100(3) |
| 3 | 10(2) | 44(2) | — | 15(2) | 0 | 70 | — | 0 | 10(2) | 90 |
| 4 | 95(2) | 82(2) | — | 38(2) | 0 | 85 | — | 0 | 5(2) | 90 |
| 5 | 80 | 0 | — | 5 | 0 | 0 | — | 0 | 0 | — |
| 6 | 80 | 70 | — | 85 | 35 | 93 | — | 70 | 0 | — |
| 7 | 100 | 83 | — | 74 | 100 | 95 | — | 70 | 60 | — |
| 8 | 99 | 95 | — | 90 | 0 | 90 | — | 0 | 30 | — |
| 9 | 100 | 87 | — | 44 | 0 | 65 | — | 50 | 0 | — |
| 10 | 99 | 82 | — | 93 | 0 | 55 | — | 75 | 0 | — |
| 11 | 92 | 99 | — | 88 | 0 | 0 | — | 0 | 40 | — |
| 12 | 93 | 0 | 82 | 0 | 0 | 0 | — | 0 | 30 | — |
| 13 | 100 | 0 | — | 52 | 0 | — | — | 60 | — | — |
| 14 | 100 | 80 | — | 63 | 40 | — | — | 60 | — | — |
| 15 | 75 | 0 | — | 90 | 0 | — | — | 0 | 0 | — |
| 16 | 75 | 75 | — | 0 | 0 | — | — | 0 | 0 | — |
| 17 | 95 | 95 | — | 0 | 80 | — | — | 50 | 80 | — |
| 18 | 95 | 75 | — | 0 | 100 | — | — | 80 | 80 | — |
| 19* | 100 | — | — | 0 | 0 | — | — | 0 | 0 | — |
| 20* | 100 | — | — | 0 | 0 | — | — | 0 | 0 | — |
| 21* | 100 | — | — | 80 | 0 | — | — | 0 | 90 | — |

Number in parentheses is number of tests done and % disease control is mean of these tests. If no # in ( ), then reported data is of 1 test.
— not tested.
*tested at 100 ppm.

TABLE 4

| Compound (100 ppm) | Percent Disease Control | | | | | |
|---|---|---|---|---|---|---|
| | WPM | WLR | RB | RSB | TLB | CDM |
| 22 | 0 | 0 | 0 | 0 | 0 | 100 |
| 23 | 0 | 0 | 0 | 0 | 0 | 99 |
| 24 | 0 | 50 | 0 | 0 | 0 | 0 |
| 25 | 75 | 0 | 0 | 0 | 0 | 0 |
| 26 | 50 | 0 | 0 | 0 | 90 | —[1] |
| 27 | 100 | 0 | 80 | 0 | 0 | — |
| 28 | 99 | 0 | 90 | 0 | 0 | — |
| 29 | 100 | — | — | 0 | 90 | — |
| 30 | 0 | 0 | 80 | 0 | 0 | 0 |
| 31 | 0 | 0 | 80 | 0 | 0 | 0 |
| 32 | 0 | 0 | 0 | 95 | 0 | 0 |
| 33 | 75 | 0 | 0 | 0 | 0 | 50 |
| 34 | 50 | 0 | 0 | 0 | 0 | 0 |
| 35 | 50 | 0 | 0 | 0 | 0 | 0 |
| 36 | 75 | 0 | 80 | 0 | 0 | — |
| 37 | 95 | 0 | 80 | 0 | 0 | — |
| 38 | 95 | 0 | 50 | 0 | 0 | — |
| 39 | 85 | 0 | 80[2] | 0 | 0 | — |
| 40 | 90 | 0 | 0 | 0 | 0 | — |
| 41 | 80 | 0 | 80 | 0 | 0 | — |
| 42 | 99 | 0 | 80 | 0 | 0 | — |
| 43 | 90 | 0 | 80 | 0 | 0 | — |
| 44 | 90 | 0 | 80 | 0 | 0 | — |
| 45 | 90 | 0 | 100 | 0 | 80 | — |
| 46 | 80 | 0 | 100 | 0 | 50 | — |
| 47 | 80 | 0 | 80 | 0 | 90 | — |
| 48 | 85 | 50 | 100 | 0 | 90 | — |

TABLE 4-continued

| Compound (100 ppm) | Percent Disease Control | | | | | |
|---|---|---|---|---|---|---|
| | WPM | WLR | RB | RSB | TLB | CDM |
| 49 | 85 | 0 | 0 | 0 | 80 | — |
| 50 | 80 | 0 | 0 | 0 | 50 | — |
| 51 | 95 | 0 | 0 | 0 | 0 | — |
| 52 | 90 | 0 | 0 | 80 | 0 | — |
| 54 | 85 | 0 | 0 | 0 | 0 | — |
| 55 | 100 | 0 | 0 | 0 | 0 | — |
| 56 | 95 | 0 | 0 | 0 | 0 | — |
| 57 | 100 | 0 | 90 | 0 | 0 | — |
| 58 | 99 | 0 | 50 | 0 | 0 | — |
| 59 | 100 | 50 | 0 | 80 | 0 | — |
| 60 | 85 | 0 | 0 | 0 | 0 | — |
| 61 | 100 | 90[2] | 50 | 0 | 0 | — |
| 62 | 99 | 0 | 0 | 0 | 0 | — |
| 63 | 100 | 90 | 0 | 0 | 0 | — |
| 64 | 99 | 0 | 90 | 0 | 0 | — |
| 65 | 100 | 50 | 80 | 0 | 0 | — |
| 66 | 95 | 0 | 90 | 0 | 0 | — |
| 67 | 100 | 0 | 90 | 0 | 80 | — |
| 68 | 100 | 0 | 80 | 0 | 80 | — |
| 69 | 100 | 0 | 90 | 0 | 0 | — |
| 70 | 100 | 80 | 0 | 0 | 95 | — |

[1]Not tested.
[2]Compound tested at 25 ppm.

What is claimed is:

1. A 2-cyano(pyridyl)ethane compound of the formula

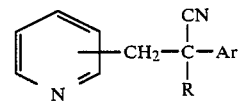

wherein R is, $(C_1-C_8)$alkyl, $(C_3-C_6)$cycloalkyl, halo$(C_1-C_8)$alkyl, $(C_3-C_6)$alkenyl, halo$(C_3-C_6)$alkenyl, $(C_3-C_6)$alkynylalkynyl, alkenyl or dialkenyl having from four to ten carbon atoms, alkoxy, alkyl or halo(alkoxyalkyl) having up to a total of eight carbon atoms, phenyl, phenyl$(C_1-C_4)$alkyl, phen$(C_2-C_4)$alkenyl, phenoxy-$(C_1-C_6)$alkyl, heterocyclic group selected from pyridyl, pyrimidyl, furyl and pyrazinyl or a heterocyclic $(C_1-C_4)$alkyl group wherein the heterocycle moiety is pyridyl, pyrimidyl, pyrazinyl, morpholinyl, pyrolyl, pyrazolyl, furyl, tetrahydrofuryl or dioxalyl, and wherein R is a phenyl, phenylalkyl, phen($C_2$-$C_4$)alkenyl or phenoxyalkyl group, the phenyl portion may be optionally substituted with up to two substituents each independently selected from halogen, nitro, trihalomethyl, cyano, ($C_1$-$C_4$)alkyl, ($C_1$-$C_4$)alkoxy, alkoxyalkyl having up to a total of four carbon atoms, ($C_1$-$C_4$)alkylthio, ($C_1$-$C_4$)alkylsulfinyl and ($C_1$-$C_4$)alkylsulfonyl groups; and Ar is a phenyl or naphthyl group wherein the phenyl is optionally substituted with up to three substituents and wherein the naphthyl is optionally substituted with up to two substituents and the substituents for the phenyl and naphthyl group are each independently selected from halogen, ($C_1$-$C_4$)alkyl, ($C_1$-$C_4$(alkoxy, alkoxyalkyl having up to a total of four carbon atoms, nitro, halomethyl, ($C_1$-$C_4$)alkylthio, ($C_1$-$C_4$)alkylsulfinyl, ($C_1$-$C_4$)alkylsulfonyl and phenyl which may be substituted with up to one substituent selected from a ($C_1$-$C_4$)alkyl, ($C_3$-$C_4$)cycloalkyl, halo($C_1$-$C_4$)alkyl, ($C_2$-$C_4$)alkenyl, ($C_2$-$C_4$)alkynyl or alkoxyalkyl having up to four carbon atoms; and its acid salts, free bases and metal salt complexes.

2. The compound of claim 1 wherein Ar is a phenyl group which is optionally substituted with up to two substituents each independently selected from halogen, ($C_1$-$C_4$)alkyl, $C_1$-$C_4$)alkoxy, nitro, halomethyl, ($C_1$-$C_4$)alkylthio, ($C_1$-$C_4$)alkylsulfinyl, ($C_1$-$C_4$)alkylsulfonyl, ($C_1$-$C_4$)alkylthio and phenyl which may be substituted with up to one substituent selected from a ($C_1$-$C_4$)alkyl, ($C_3$-$C_4$)cycloalkyl, halo($C_1$-$C_4$)alkyl, ($C_2$-$C_4$)alkenyl, ($C_2$-$C_4$)alkynyl or alkoxyalkyl having up to four carbons; and its acid salts, free bases and metal salt complexes.

3. The compound of claim 1 wherein R is a ($C_1$-$C_6$)alkyl, ($C_4$-$C_6$)alkenyl, ($C_4$-$C_6$)alkynyl, alkynylalkenyl or dialkenyl having from four to ten carbon atoms, halo-($C_1$-$C_6$)alkyl having up to four halogen atoms, halo($C_3$-$C_6$)alkenyl having up to two halogen atoms, alkoxyalkyl having up to six carbon atoms, phenyl, phen($C_1$-$C_3$)alkyl, phen($C_2$-$C_4$)alkenyl or phenoxy($C_2$-$C_4$)alkyl wherein the phenyl and phenyl moiety of the phenalkyl, phenalkenyl and phenoxyalkyl groups may be substituted with up to two substituents each independently selected from chlorine, bromine, fluorine, iodine, nitro, trifluoromethyl, cyano, ($C_1$-$C_4$)alkyl and ($C_1$-$C_4$)alkoxy groups; and Ar is a phenyl group or a phenyl group optionally substituted with up to two substituents each independently selected from a fluorine, chlorine, bromine, trifluoromethyl, difluoromethyl, monofluoromethyl, ($C_1$-$C_4$)alkyl, ($C_1$-$C_4$)alkoxy and phenyl groups; and its acid salts, free bases and metal salt complexes.

4. The compound of claim 3 which is a 3-pyridyl and wherein R is ($C_4$-$C_5$)alkenyl, alkoxyalkyl having up to six carbon atoms, phen($C_1$-$C_3$)alkyl, phenoxy($C_2$-$C_3$)alkyl or halo($C_1$-$C_4$)alkyl having up to three fluorine atoms or halo($C_3$-$C_6$)alkenyl having one fluorine or chlorine atom, wherein the phenyl portion of the phenalkyl or phenoxyalkyl moiety is optionally substituted with up to two substituents each independently selected from chlorine, bromine, fluorine, trifluoromethyl, cyano, methoxy and ethoxy groups; and Ar is a phenyl group optionally substituted with up to two substituents each independently selected from chlorine, bromine, trifluoromethyl, ($C_1$-$C_2$)alkoxy and phenyl groups; and its acid salts, free bases and metal salt complexes.

5. The compound of claim 4 wherein R is a alkoxyalkyl having up to six carbon atoms, phen($C_1$-$C_3$)alkyl or phenoxy($C_2$-$C_3$)alkyl wherein the phenyl portion of the phenalkyl or phenoxyalkyl moiety is optionally substituted with up to two substituents each independently selected from chlorine, bromine, fluorine, trifluoromethyl, methoxy and ethoxy groups; and Ar is a phenyl group optionally substituted with up to two substituents each independently selected from chlorine, bromine, methoxy, ethoxy and phenyl groups; and its acid salts, free bases and metal salt complexes.

6. The compound of claim 5 wherein R is a benzyl or phenethyl group wherein the phenyl portion of the benzyl or phenethyl is optionally substituted with up to two substituents each independently selected from fluorine, chlorine, methoxy and ethoxy; and Ar is a phenyl group optionally substituted with up to two substituents each independently selected from fluorine, chlorine, methoxy and ethoxy; and its acid salts, free bases and metal salt complexes.

7. The compound of claim 5 wherein R is methoxybutyl, tetrahydrofuryl, benzyl, phenethyl, 2-phenoxyethyl, 3-phenoxypropyl, methoxybenzyl, methoxyphenethyl, fluorophenyl or chlorophenyl; and Ar is phenyl, chlorophenyl, fluorophenyl, dichlorophenyl, difluorophenyl or methoxyphenyl; and its acid salts, free bases and metal salt complexes.

8. The compound of claim 6 wherein R is a benzyl or phenethyl group which is substituted with up to one substituent selected from fluoro, chloro, trifluoromethyl, methyl or methoxy and Ar is chlorophenyl, fluorophenyl or trifluoromethylphenyl, its acid salts, free bases and metal salt complexes.

9. The compound of claim 7 selected from 2-cyano2-(4-chlorophenyl)-4-phenoxy-1-(3-pyridyl)butane, 2-cyano2-(4-chlorophenyl)-4-(4-methoxyphenyl)-1-(3-pyridyl)butane, 2-cyano-2-(4-chloro- or fluoro-phenyl)-3-phenyl-1(3-pyridyl)propane, 2-cyano-2-(4-chloro- or fluorophenyl)-3-(4-methylphenyl)-1-(3-pyridyl)propane and 2-cyano-2-(4-chloro- or fluoro- phenyl)-3-(4-methoxyphenyl)-1-(3-pyridyl)propane.

10. A composition comprising
a 2-cyano(pyridyl)ethane compound of the formula

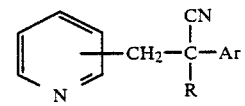

wherein R is ($C_1$-$C_8$)alkyl, ($C_3$-$C_6$)cycloalkyl, halo($C_1$-$C_8$)alkyl, ($C_3$-$C_6$)alkenyl, halo($C_3$-$C_4$)alkenyl, ($C_3$-$C_6$)alkynyl, alkynylalkenyl or dialkenyl having from four to ten carbon atoms, alkoxyalkyl or halo(alkoxyalkyl) having up to a total of eight carbon atoms, phenyl, phenyl($C_1$-$C_4$)alkyl, phen($C_2$-$C_4$)alkenyl, phenoxy ($C_1$-$C_6$)alkyl, heterocyclic group selected from pyridyl, pyrimidyl, furyl and pyrazinyl or a heterocyclic ($C_1$-$C_4$)alkyl group wherein the heterocycle moiety is pyridyl, pyrimidyl, pyrazinyl, morpholinyl, pyrolyl, pyrazolyl, furyl, tetrahydrofuryl or dioxalyl, and when R is a phenyl, phenylalkyl, phen($C_2$-$C_4$)alkenyl or phenoxylalkyl group, the phenyl portion may be optionally substituted with up to two substituents each independently selected from halogen, nitro, trihalomethyl, cyano, ($C_1$-$C_4$)alkyl, ($C_1$-$C_4$)alkoxy, alkoxyalkyl having up to a total of four carbon atoms, ($C_1$-$C_4$)alkylthio, ($C_1$-$C_4$)alkylsulfinyl and ($C_1$-$C_4$)alkylsulfonyl groups; and Ar is a phenyl or naphthyl group wherein the phenyl is optionally substituted with up to three substituents and wherein the naphthyl is optionally substituted with up to two substituents and the substituents for the phenyl and naphthyl group are each independently selected from halogen, ($C_1$-$C_4$)alkyl, ($C_1$-$C_4$)alkoxy, alkoxyalkyl having up to a total of four carbon atoms, nitro, halomethyl, ($C_1$-$C_4$)alkylthio, ($C_1$-$C_4$alkylsulfinyl, ($C_1$-$C_4$)alkylsulfonyl and phenyl which may be substituted with up to one substituent selected from a ($C_1$-$C_4$)alkyl, ($C_3$-$C_4$)cycloalkyl, halo($C_1$-$C_4$)alkyl, ($C_2$-$C_4$) alkyl, ($C_2$-$C_4$alkynyl or alkoxyalkyl having up to four carbon atoms; and its acid salts, free bases and metal salt complexes in a fungicidally-effective amount and an agronomically-acceptable carrier.

11. A composition comprising a compound of claim 4 in a fungicidally-effective amount and an agronomically-acceptable carrier.

12. A composition comprising a compound of claim 6 in a fungicidally-effective amount and an agronomically-acceptable carrier.

13. A composition comprising a compound of claim 8 in a fungicidally-effective amount and an agronomically-acceptable carrier.

14. A method for controlling a fungus comprising applying to the fungus or its habitat a fungicidally-effective amount of a 2-cyano(pyridyl)ethane compound of the formula

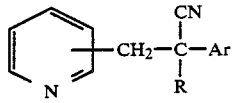

wherein R is a hydrogen, ($C_1$-$C_8$)alkyl, ($C_3$-$C_6$)cycloalkyl, halo($C_1$-$C_8$)alkyl, ($C_3$-$C_6$)alkenyl, halo($C_3$-$C_6$)alkenyl, ($C_3$-$C_6$)alkynyl, alkynylalkenyl or dialkenyl having from four to ten carbon atoms, alkoxyalkyl or halo(alkoxyalkyl) having up to a total of eight carbon atoms, phenyl, phenyl ($C_1$-$C_4$)alkyl, phen($C_2$-$C_4$)alkenyl, phenoxy ($C_1$-$C_6$)alkyl, heterocyclic group selected from pyridyl, pyrimidyl, furyl and pyrazinyl or a heterocyclic ($C_1$-$C_4$)alkyl group wherein the heterocycle moiety is pyridyl, pyrimidyl, pyrazinyl, morpholinyl, pyrolyl, pyrazolyl, furyl, tetrahydrofuryl or dioxalyl, and when R is a phenyl, phenylalkyl, phen ($C_2$-$C_4$)alkenyl or phenoxyalkyl group, the phenyl portion may be optionally substituted with up to two substituents each independently selected from halogen, nitro, trihalomethyl, cyano, ($C_1$-$C_4$)alkyl, $C_1$-$C_4$)alkoxy, alkoxyalkyl having up to a total of four carbon atoms, ($C_1$-$C_4$)alkylthio, ($C_1$-$C_4$)alkylsulfinyl and ($C_1$-$C_4$)alkylsulfonyl groups; and Ar is a phenyl or naphthyl group wherein the phenyl is optionally substituted with up to three substituents and wherein the naphthyl is optionally substituted with up two substituents for the phenyl and naphthyl group are each independently selected from halogen, ($C_1$-$C_4$)alkyl, ($C_1$-$C_4$)alkoxy, alkoxyalkyl having up to a total of four carbon atoms, nitro, halomethyl, ($C_1$-$C_4$)alkylthio, ($C_1$-$C_4$)alkylsulfinyl, ($C_1$-$C_4$)alkylsulfonyl and phenyl which may be substituted with up to one substituent selected from a ($C_1$-$C_4$)alkyl, ($C_3$-$C_4$)cycloalkyl, halo($C_4$-$C_4$)alkyl, ($C_2$-$C_4$)alkenyl, ($C_2$-$C_4$)alkynyl or alkoxyalkyl having up to four carbon atoms; and its acid salts, free bases and metal salt complexes.

15. A method for controlling a phytopathogenic fungus comprising applying to the fungus or its habitat a fungicidally-effective amount of a compound of claim 4.

16. A method for controlling a phytopathogenic fungus comprising applying to the fungus or its habitat a fungicidally-effective amount of a compound of claim 6.

17. A method for controlling a phytopathogenic fungus comprising applying to the fungus or its habitat a fungicidally-effective amount of a compound of claim 8.

18. The compound of claim 1 wherein Ar is a phenyl group substituted one or two halogen atoms and R is an unsubstituted phenethyl group, a 2-tetrahydrofurylalkyl group, a ($C_3$-$C_6$) haloalkenyl group or an ($C_3$-$C_6$)alkynyl group.

19. The compound of claim 18 wherein Ar is a phenyl group substituted one or two substituents each selected from fluorine or chlorine atom and R is an unsubstituted phenethyl group, 2-tetrahydrofurylmethyl group, 1-(2-chloro- or fluoro-)propen-2-yl, or propyn-3yl group.

* * * * *